US006868963B2

(12) United States Patent
Borovsky (10) Patent No.: US 6,868,963 B2
(45) Date of Patent: Mar. 22, 2005

(54) CONTACT LENS CLEANING AND STORAGE CASE WITH CONTAMINANT SEPARATION

(76) Inventor: Simcha Borovsky, 17-25 Hunter Pl., Fair Lawn, NJ (US) 07410

( * ) Notice: Subject to any disclaimer, the term of this patent is extended or adjusted under 35 U.S.C. 154(b) by 0 days.

(21) Appl. No.: 10/348,625

(22) Filed: Jan. 22, 2003

(65) Prior Publication Data

US 2004/0140229 A1 Jul. 22, 2004

(51) Int. Cl.[7] .............................................. A45C 11/04
(52) U.S. Cl. ...................................................... 206/5.1
(58) Field of Search .............................. 206/5.1, 316.1, 206/454, 811, 524.1, 524.3; 134/184, 186, 901

(56) References Cited

U.S. PATENT DOCUMENTS

| 3,035,589 | A |   | 5/1962  | King                    |
|-----------|---|---|---------|-------------------------|
| 3,460,552 | A | * | 8/1969  | Sturgeon ......... 206/5.1 |
| 3,695,280 | A | * | 10/1972 | Sturgeon ......... 206/5.1 |
| 3,856,571 | A | * | 12/1974 | Sherman ......... 206/5.1 |
| 5,080,839 | A |   | 1/1992  | Kindt-Larsen            |
| 5,176,159 | A |   | 1/1993  | Yoshihara et al.        |
| 5,195,549 | A |   | 3/1993  | Adams                   |
| 5,431,879 | A | * | 7/1995  | Heyl et al. ....... 206/5.1 |
| 6,432,217 | B1|   | 8/2002  | Baxter et al.           |

* cited by examiner

Primary Examiner—Mickey Yu
Assistant Examiner—J. Gregory Pickett
(74) Attorney, Agent, or Firm—Richard M. Goldberg (57) ABSTRACT

A contact lens cleaning and storage case includes a base having two container sections for holding a liquid; two lens holders, each positioned above a lower wall of a respective container section and each at least partially sitting within the respective container section, each lens holder having a bottom wall; a drain connected to the bottom of each lens holder for draining liquid from each lens holder to the container sections, the drain including reduced diameter openings for restricting a liquid flow rate so as to provide that liquid drainage from the lens holders to the container sections occurs in a time of ten to fifteen seconds; additional openings which provide fluid communication between atmosphere and the container sections so as to provide for displacement of air in the container sections; and two caps, each for removably covering a respective lens holder.

33 Claims, 9 Drawing Sheets

CONTACT LENS CLEANING AND STORAGE CASE WITH CONTAMINANT SEPARATION

BACKGROUND OF THE INVENTION

The present invention relates generally to contact lens cases, and more particularly, is directed to a contact lens cleaning and storage case with an arrangement for separating contaminants away from the stored lens.

It is know to provide contact lens cases for storing and cleaning contact lenses. Generally, such known contact lens cases include a base with two wells or compartments, each for holding a contact lens and cleaning liquid and/or saline solution therein, along with a threaded cover for each well which is removably screwed onto the base in covering relation to each respective well.

However, when a contact lens is placed in a well along with a cleaning solution, the contaminants on the lens remain in the same well in contact with the contact lens. This means that the contact lens is not effectively cleaned of the contaminants. When the lens is removed to place it in a person's eye, many of the contaminants, including protein and bacteria remain on the contact lens and spoil the fresh solution. A person thereby starts the next day with contaminated lenses. This affects the wearing life of the contact lens, as well as the comfort to the wearer and the clarity of the lens.

Further, if the lens deposits are not properly washed away from the lens surface, the deposits may bond to the lens permanently, causing wearer discomfort and frequent lens replacement. Further, a non-cleaned lens, when left in the storage case overnight can harbor bacteria, helping microorganisms to thrive, and thereby risking eye infection.

SUMMARY OF THE INVENTION

Accordingly, it is an object of the present invention to provide a contact lens cleaning and storage case that overcomes the problems with the aforementioned prior art.

It is another object of the present invention to provide a contact lens cleaning and storage case with an arrangement for separating contaminants away from the stored lens.

It is still another object of the present invention to provide such a contact lens cleaning and storage case that requires the cleaning solution to wash over the contact lens for a predetermined period and then drain to a different location, along with the contaminants.

It is yet another object of the present invention to provide a contact lens cleaning and storage case in which the contaminants will not return to contaminate the stored contact lens in the case, even if the case is turned upside down.

It is a further object of the present invention to provide a contact lens cleaning and storage case that reduces the risk of ocular infections.

It is a still further object of the present invention to provide a contact lens cleaning and storage case that improves contact lens wearer comfort.

It is a yet further object of the present invention to provide a contact lens cleaning and storage case that improves visual clarity through the contact lens.

It is another object of the present invention to provide a contact lens cleaning and storage case that is easy and economical to manufacture and use.

In accordance with an aspect of the present invention, a contact lens cleaning and storage case includes a base having at least one container section therein for holding a liquid; at least one lens holder positioned above a lower wall of the at least one container section, each lens holder having a lower section; a drain arranged in the lower section of each lens holder for draining liquid from the at least one lens holder to the at least one container section; and at least one cap for removably covering the at least one lens holder.

The at least one lens holder at least partially sits within the at least one container section, and is secured to the base.

Each lens holder includes a bowl shaped member for holding a contact lens, and the drain includes a drain tube extending from a bottom of the bowl shaped member. Specifically, the drain includes a drain tube extending from the lower section of each lens holder. In one embodiment, the drain tube includes a plurality of openings therein. In another embodiment, the lower section of the lens holder includes a plurality of openings, and the drain tube is connected to the lower section in surrounding relation to the plurality of openings. In either case, the plurality of openings have diameters that restrict a flow rate of liquid therethrough so as to prevent draining of liquid from the at least one lens holder to the at least one container section in a time less than a predetermined time, for example, in a range between approximately ten and fifteen seconds.

Further, the at least one lens holder includes at least one drain opening which provides fluid communication between atmosphere and the at least one container section. In one embodiment, the at least one lens holder includes a bowl shaped member for holding a contact lens and a peripheral flange connected to the bowl shaped member in order to connect the at least one lens holder to the base, with the at least one drain opening being provided in the peripheral flange. In this case, in order to secure the at least one lens holder to the base, the base includes at least one recess and the at least one lens holder includes at least one catch mounted to the peripheral flange for engaging in the at least one recess in order to secure the at least one lens holder to the base. In another embodiment, the base has an upper surface, and the at least one lens holder has a lower surface in flush engagement with the upper surface and secured thereto. In this case, the at least one lens holder includes a peripheral wall that extends at least partially above the lower surface and at least one drain opening which provides fluid communication between atmosphere and the at least one container section being provided through the peripheral wall. In either case, the at least one cap blocks the at least one drain opening when covering the respective lens holder.

In accordance with another aspect of the present invention, a contaminant separator for use with a contact lens cleaning and storage case of the type including a base having at least one container section therein for holding a liquid, and at least one cap, includes a lens holder adapted to be positioned above a lower wall of the at least one container section, each lens holder having a lower section; and a drain arranged in the lower section of each lens holder for draining liquid from the at least one lens holder to the at least one container section.

The above and other objects, features and advantages of the invention will become readily apparent from the following detailed description thereof which is to be read in connection with the accompanying drawings.

DETAILED DESCRIPTION

Referring to the drawings in detail, and initially to FIGS. 1–6, a small, portable, contact lens cleaning and storage case 10 according to a first embodiment of the present invention, is made of a molded plastic material or any other liquid impermeable material, and includes a base 12, two separator inserts 14 positioned in base 12, and caps 16.

Figure 1:
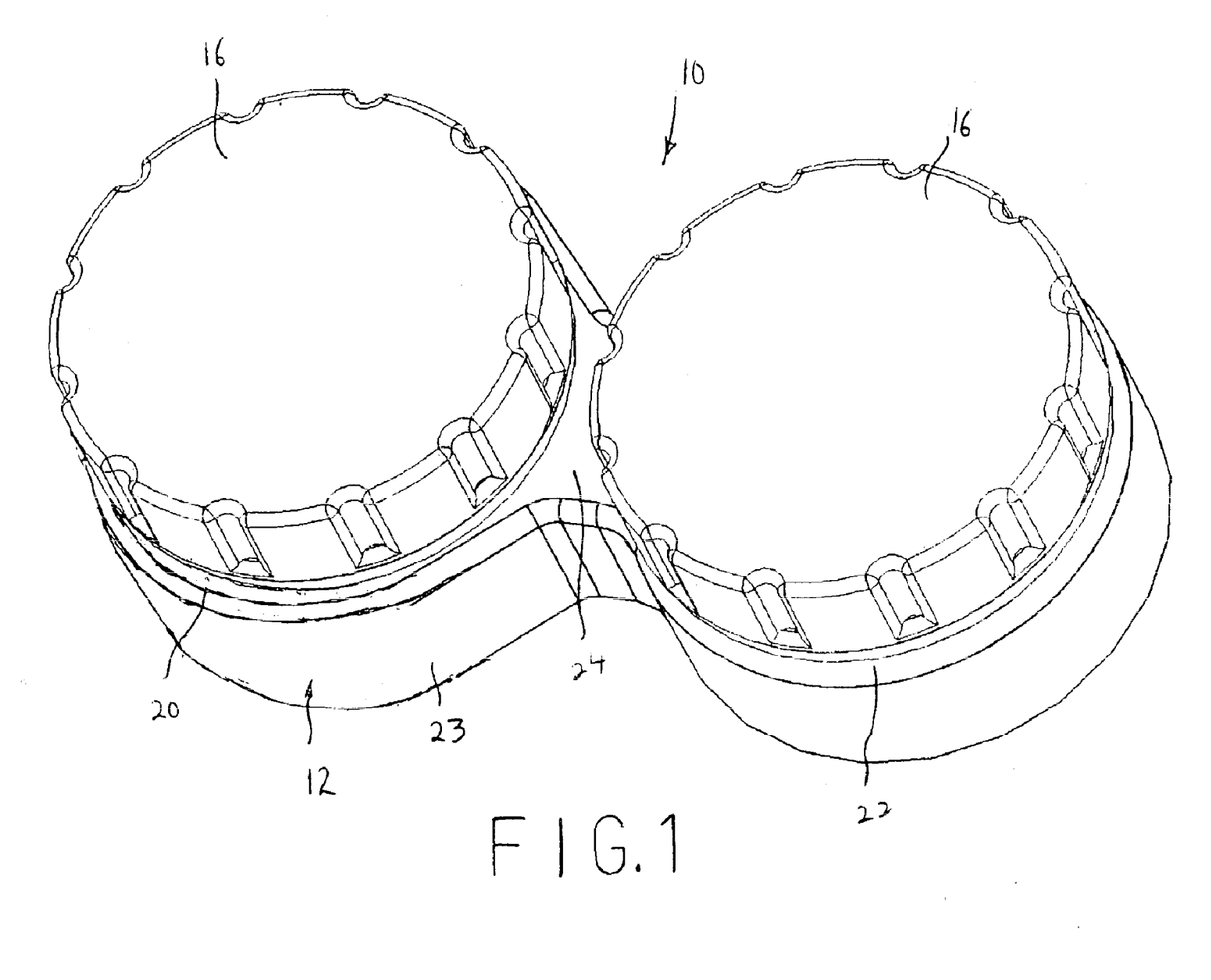
FIG. 1 is a perspective view of a contact lens cleaning and storage case according to a first embodiment of the present invention.
Figures 3, 4:
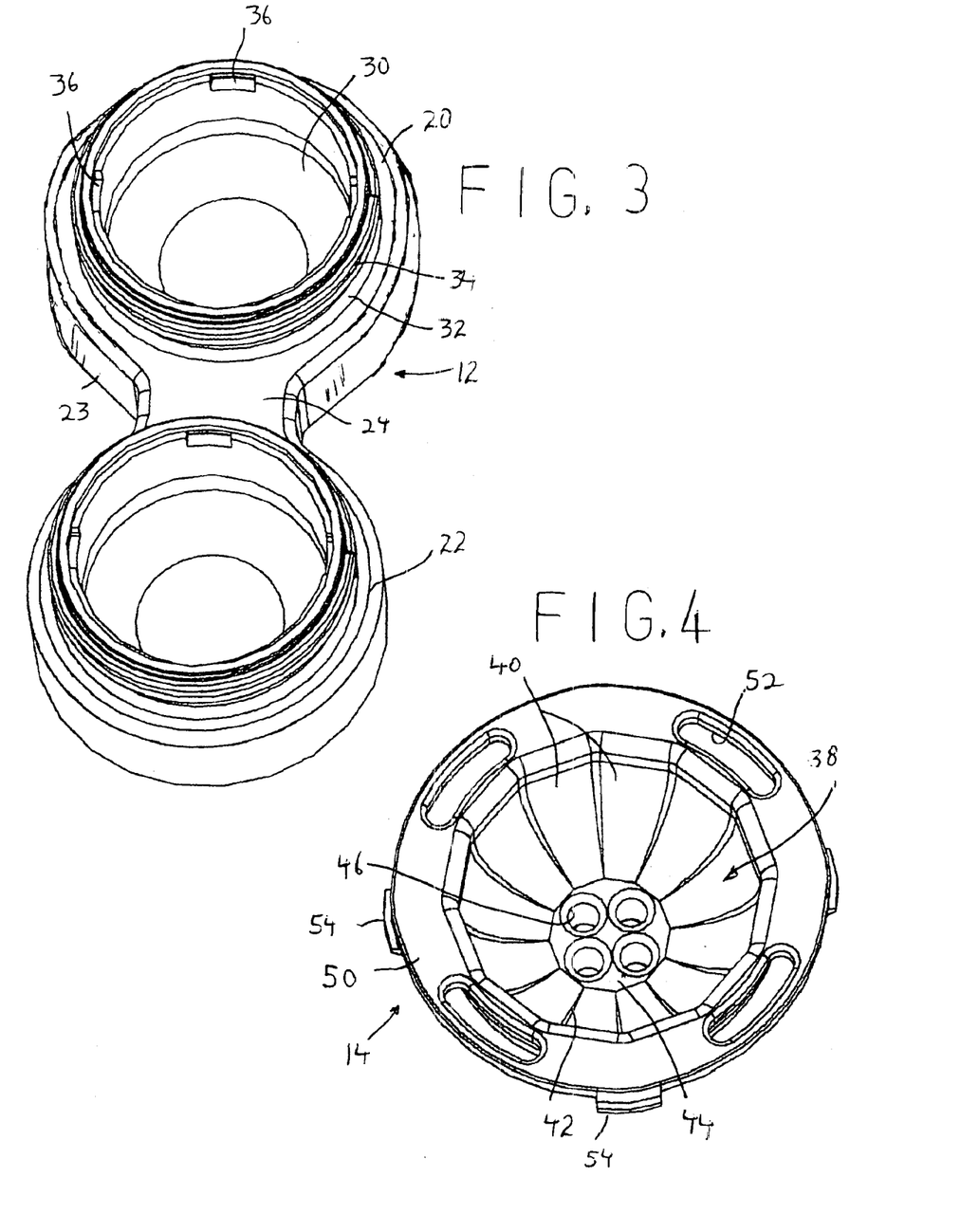
FIG. 3 is a top perspective view of the base of the contact lens cleaning and storage case.
FIG. 4 is a top perspective view of the separator insert of the contact lens cleaning and storage case.

Base 12 includes an oblong plate 18 having a general shape of the number "8" and being of a generally constant thickness. Specifically, oblong plate 18 includes a circular left section 20, a circular right section 22 and a reduced width center connecting section 24 which connects together left section 20 and right section 22 and which has a width less than the diameters of left section 20 and right section 22. A skirt 23 of a constant height is integrally molded at the periphery of oblong plate 18 and extends down therefrom in order to support case 10 on a surface.

Figure 2:
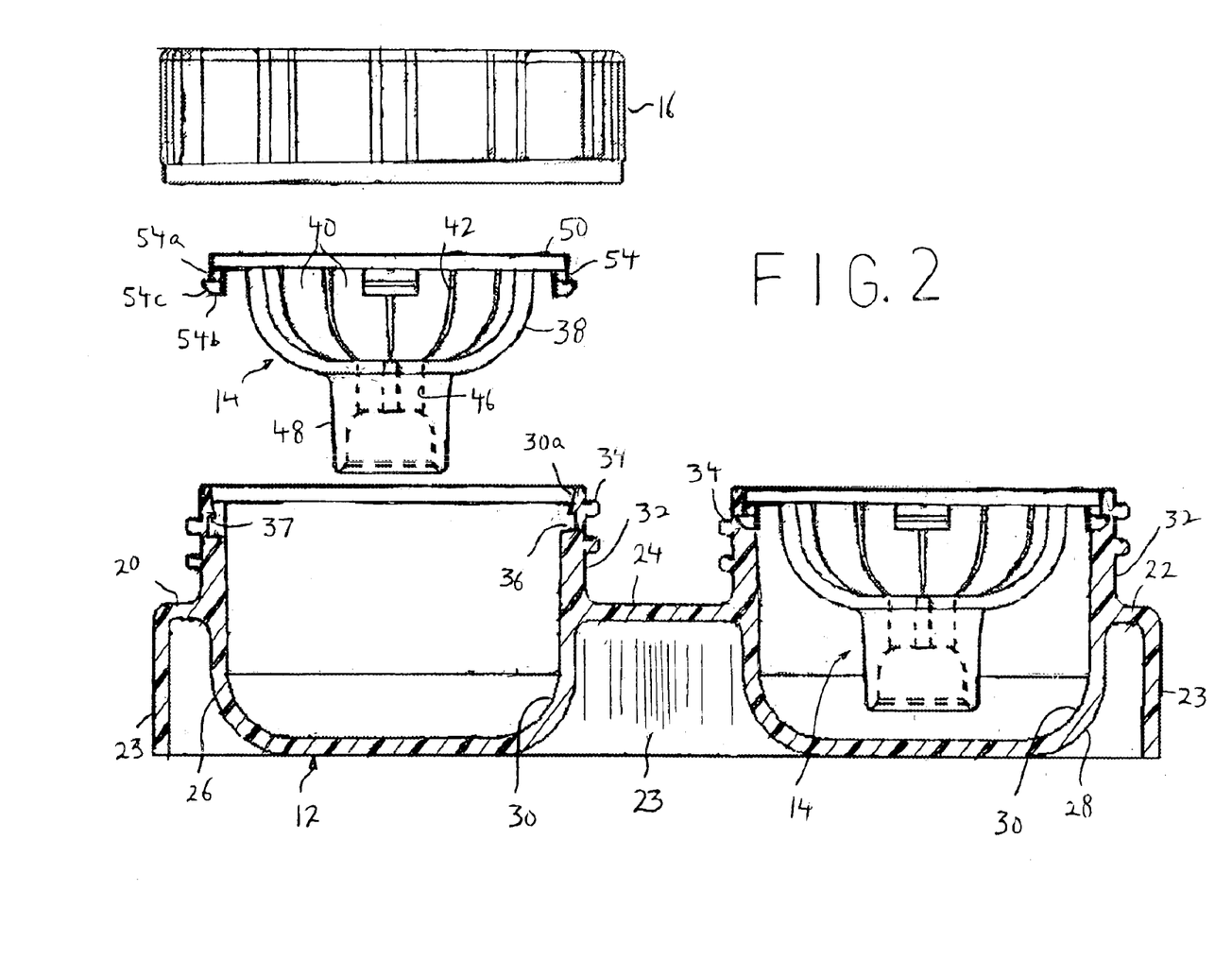
FIG. 2 is a blown-apart side elevational view, partly in cross-section, of the contact lens cleaning and storage case.

A molded cup-shaped container 26 is formed in left section 20 and a similar molded cup-shaped container 28 is formed in right section 22, both extending upwardly and downwardly from oblong plate 18, as shown best in FIG. 2, each forming a well for holding liquid therein.

Containers 26 and 28 are preferably identical in construction, and in this regard, each container 26 and 28 has a generally cylindrical configuration with a radius in the range of approximately 2.0 to 3.0 cm and a height in the range of approximately 0.5 to 2.0 cm. Each container 26 and 28 further includes a smooth, bowl-like interior wall 30, and an exterior annular wall 32 with threads 34 formed on the portion of exterior annular wall 32 that extends above oblong plate 18.

In addition, a plurality of equiangularly spaced recessed sections 36, for example, four in number, are formed below the upper end of interior wall 30. Interior wall 30 has an inward sloped portion 30a extending from the upper edge thereof to each recessed section 36, and thereby forms a shoulder 37 at the intersection of inward sloped portion 30a and recessed section 36, the purpose for which will become apparent from the description hereinafter.

Figure 5:
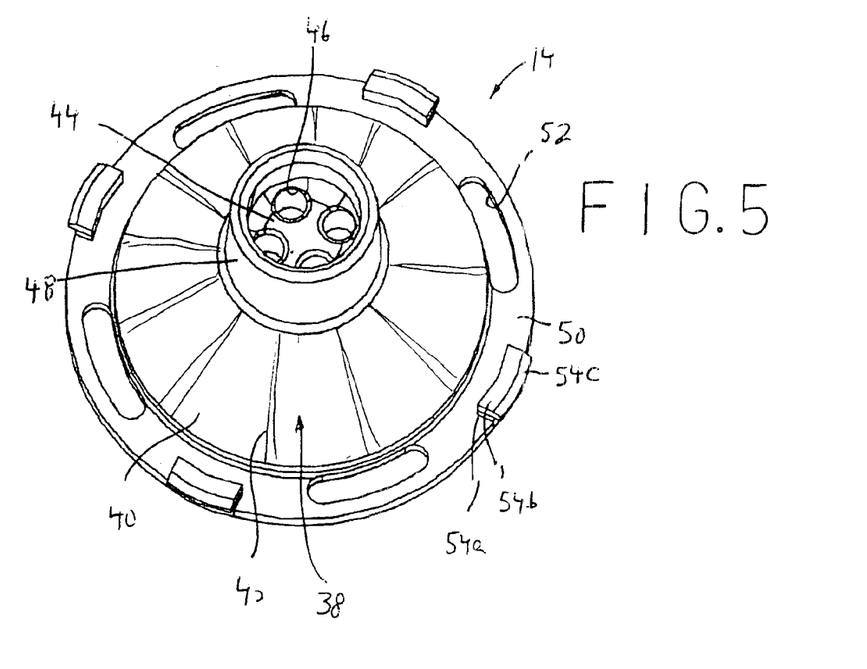
FIG. 5 is a bottom perspective view of the separator insert of the contact lens cleaning and storage case.

The two separator inserts 14 positioned in base 12, are each formed identically, and specifically, each is snap fitted within a respective container 26 and 28. Each insert 14 includes a generally frusto-conical bowl shaped member 38 with gently sloping down curved walls. Preferably, as shown in FIGS. 2, 4 and 5, member 38 is formed by a plurality of gently sloping down sections 40 connected together at their vertical edges. Although twelve such sections 40 are shown in FIGS. 4 and 5, the present invention is not limited thereby. As shown, each section 40 is curved slightly in the circumferential direction and in the vertical direction. Accordingly, there are raised vertical discontinuity lines 42 at the inner surface of member 38 between sections 40, which function to prevent the contact lenses usually stored in a liquid disinfectant from adhering to the interior wall of bowl shaped member 38. However, the present invention is not limited thereby, and the interior wall of bowl shaped member 38 can be entirely smooth throughout.

The lower open end of bowl shaped member 38 is closed by a lower wall 44, which has a plurality of small drain openings 46. Although four drain openings are shown, the present invention is not limited thereby. As will be understood from the discussion which follows, the diameters of drain openings 46 are such that liquid disinfecting solution placed in bowl shaped member 38 will take approximately ten to fifteen seconds to drain, thereby providing sufficient time to clean the contact lens therein.

A drain tube 48 is molded to the lower end of bowl shaped member 38 in surrounding relation to lower wall 44 such that liquid from small drain openings 46 drains through drain tube 48.

An upper annular ledge 50 is molded to the upper end of bowl shaped member 38 and extends radially outwardly therefrom. Four elongated openings 52 are equiangularly formed in ledge 50. In addition, four equiangularly spaced, L-shaped catches 54 extend down and then radially outward from the outer edge of ledge 50. Specifically, each catch 54 includes a first leg 54a that extends down from the lower surface of ledge 50 and a second leg 54b that extends radially outward from the lower end of first leg 54a. The radially outer surface 54c of second leg 54b has a downward and inward slope. Accordingly, when separator insert 14 is positioned within a cup-shaped container 26 or 28, sloped outer surfaces 54c ride along sloped portions 30a and are thereby forced radially inward. As the upper ends of sloped outer surfaces 54c ride down past the lower edges of sloped portions 30a, the spring pressure caused by the bending of catches 54 causes second legs 54b to engage within recessed sections 36, whereby they are locked in place by shoulders 37 engaging the upper surfaces of second legs 54b, thereby to lock separator insert 14 in the respective cup-shaped container 26 or 28.

Figure 6:
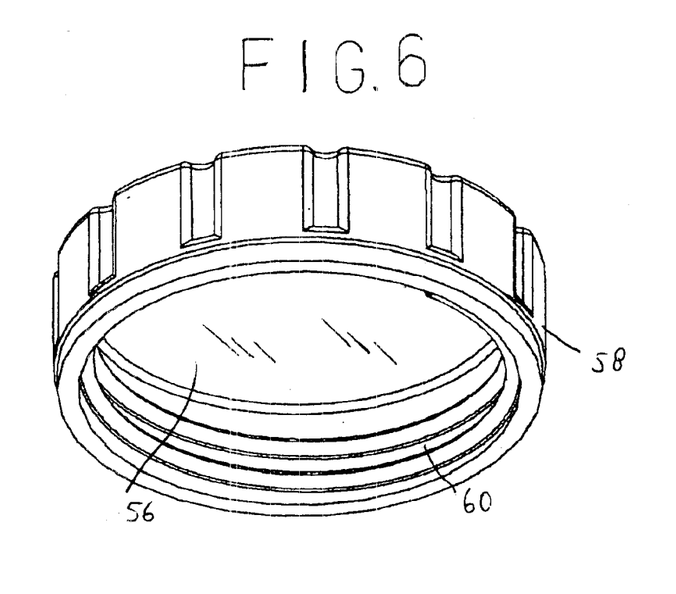
FIG. 6 is a bottom perspective view of the cap of the contact lens cleaning and storage case.

Each cap 16 includes a circular top wall 56 and an annular skirt 58 which extends downwardly from the outer edge of top wall 56. The inner surface of skirt 58 includes threads 60 which mate with threads 34 so that each cap 16 can be threadedly received on cup-shaped container 26 or 28 in a sealing manner, as is well known in the art. When a cap 16 is threaded on a cup-shaped container 26 or 28, the lower edge of cap 16 sits on ledge 50 and seals elongated openings 52.

Figure 12:
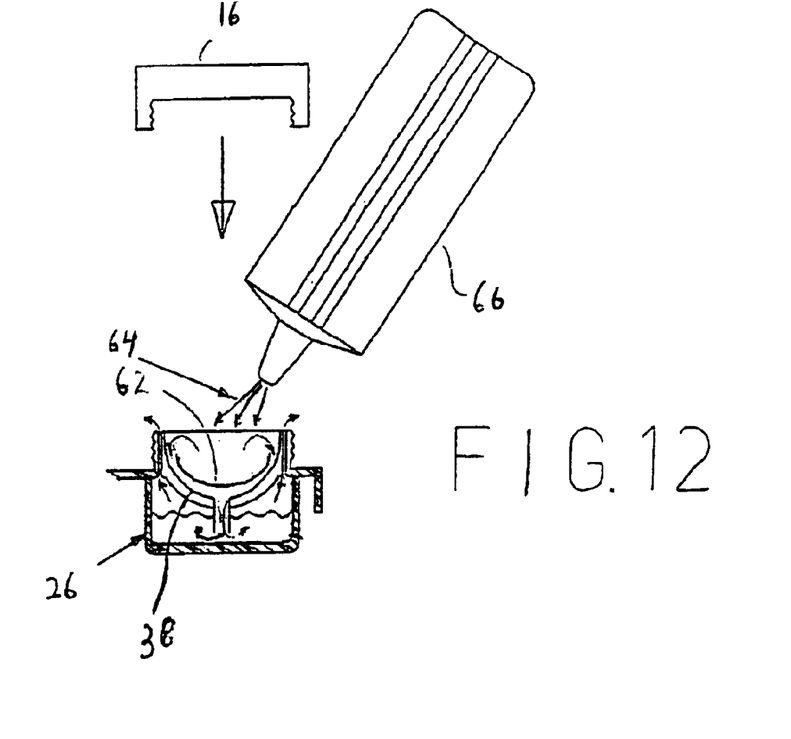
FIG. 12 is a schematic cross-sectional view, showing the operation of adding cleaning solution.
Figure 13:
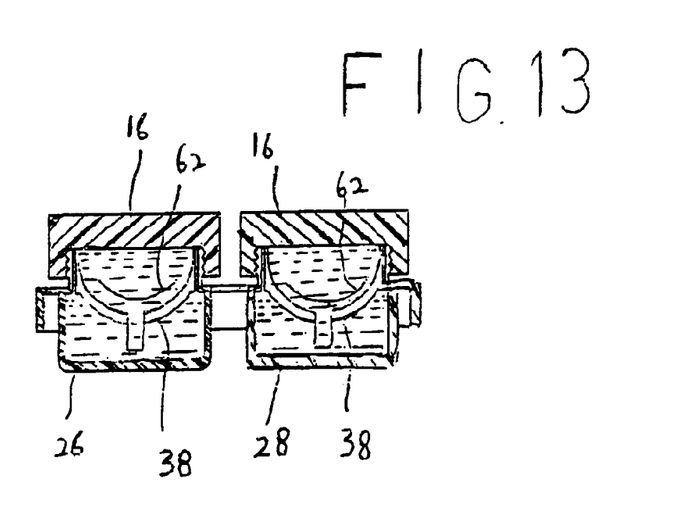
FIG. 13 is a schematic cross-sectional view, showing the closed case with the cleaning solution therein.

Referring now to FIGS. 12 and 13, in operation, a contact lens 62 is placed within bowl shaped member 38, and disinfecting liquid 64 from a container 66 is supplied to cup-shaped container 26. This functions to provide a strong cleaning and rinsing of contact lens 62. The high-pressure rinsing from squeezing container 66 results in a thorough rinsing of the contact lens. Because of the small diameter of openings 46, the rinse takes approximately ten to fifteen seconds before the liquid drains to cup-shaped container 26 through drain tube 48. Any contaminants on contact lens 62 are cleaned by the liquid and travel with the liquid into cup-shaped container 26. Any air from cup-shaped container 26 is forced out through elongated openings 52, thereby permitting more solution to drain into cup-shaped container 26. As container 26 is filled and additional disinfecting liquid is provided, the new solution covers contact lens 62 and fills up bowl shaped member 38. This indicated that all cavities are full with solution, and no air is trapped therein. Caps 16 are then threaded thereon.

Because the contaminants have traveled through drain tube 48 to lower cup-shaped container 26, the liquid in bowl shaped member 38 is clear and uncontaminated. In effect, bowl shaped member 38 functions as a separator between the uncontaminated liquid at an upper level and the contaminated liquid in a lower level. Further, because bowl shaped member 38 is filled with liquid, if contact lens cleaning and storage case 10 is turned upside down after caps 16 have been threaded thereon, the liquid in bowl shaped member 38 will prevent the contaminated liquid from entering and thereby prevent the contaminated liquid from contaminating contact lens 62.

When the lenses are to be worn again, for example, the next morning, caps 16 are removed, and each contact lens 62 is removed from the uncontaminated liquid and placed in the person's eye. Because caps 16 are removed, when case 10 is turned upside down at this time, the uncontaminated liquid in bowl shaped member 38 is first drained, and there is then no resistance to drainage of the contaminated liquid, which then drains through drain tube 48 and openings 46, as well as through elongated openings 52.

Thus, with the present invention, contact lens 62 is rinsed with disinfecting liquid so that the contaminants are rinsed off contact lens 62 and taken away to a lower location, whereby contact lens 62 sits in the additional uncontaminated liquid then placed in the raised bowl shaped member 38.

In experiments performed by an independent laboratory with the present invention, it was found that the present invention removed up to 99.97% of bacteria from the lens surface.

It will be appreciated that, although separator insert 14 has been discussed as being snap fitted in cup-shaped container 26 or 28, it can be a separate element that is merely removably fitted therein without snap fitting or the like. In this manner, separator inserts 14 can be used with existing contact lens cases. In such case, stabilizing legs or the like can be provided, if desired, to provide a more stable fit in the existing contact lens case.

Referring now to FIGS. 7–11, a contact lens cleaning and storage case 110 according to a second embodiment of the present invention will now be described, in which elements common with those of contact lens cleaning and storage case 110 are identified by the same reference numerals augmented by 100.

Figure 7:
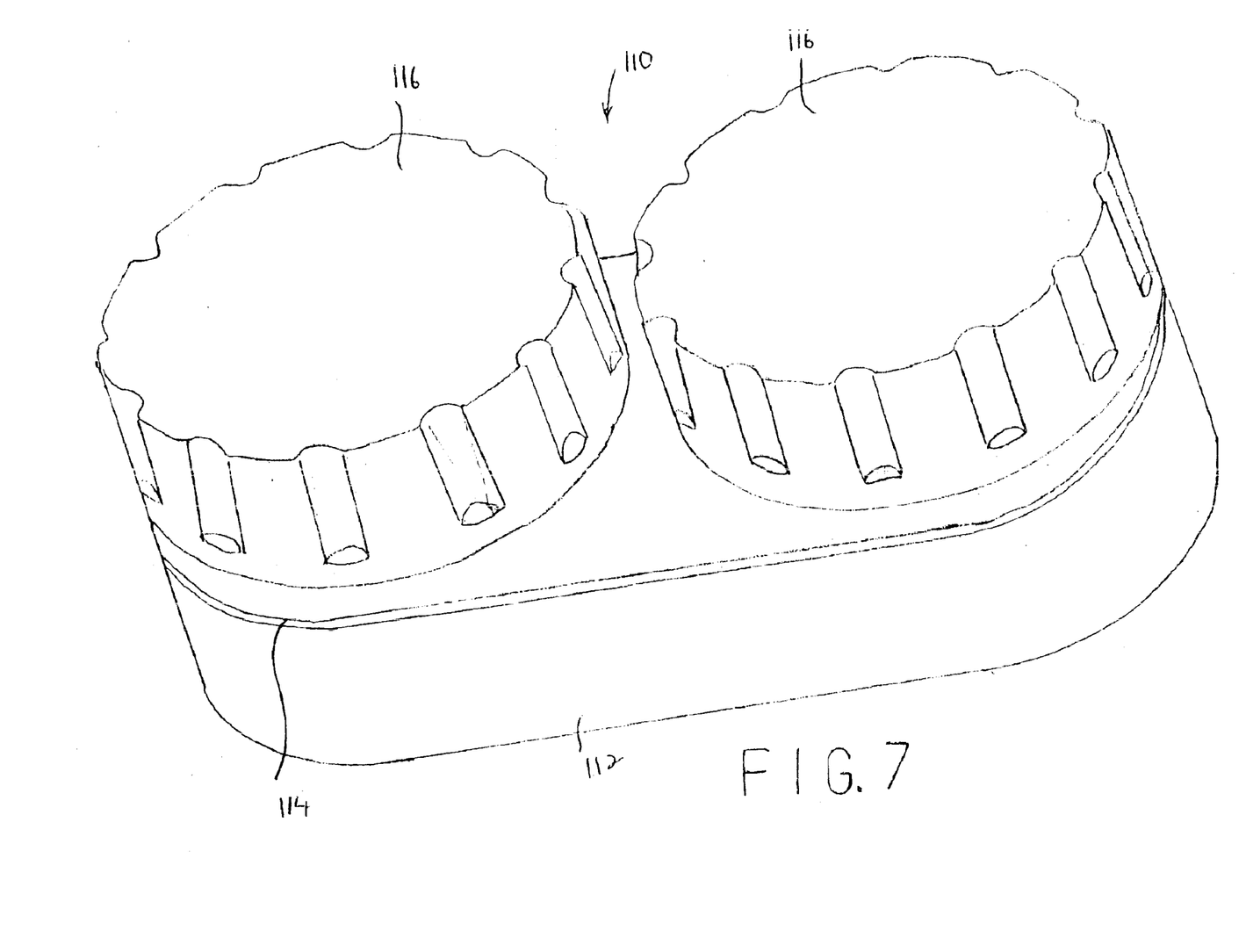
FIG. 7 is a perspective view of a contact lens cleaning and storage case according to a second embodiment of the present invention.
Figure 8:
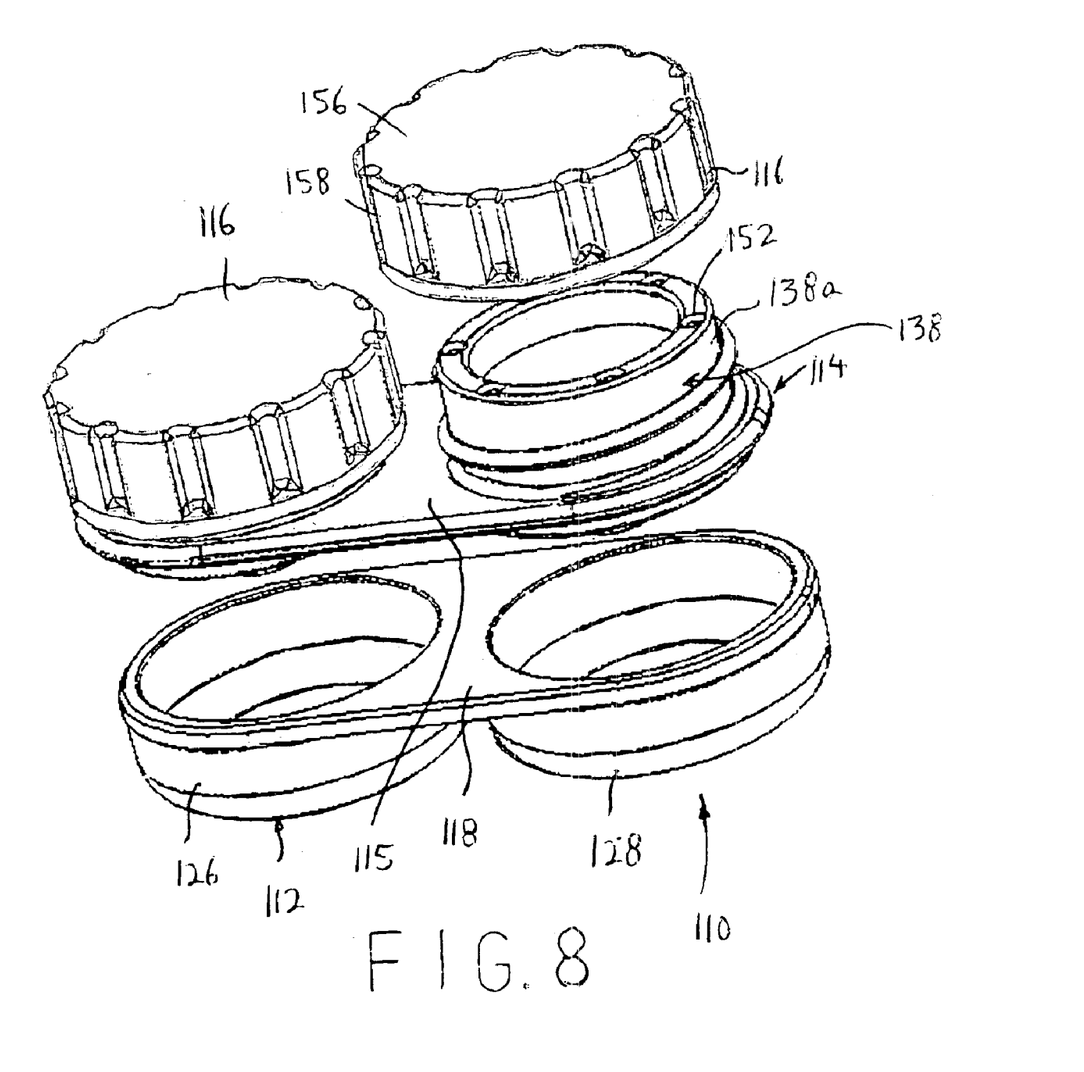
FIG. 8 is an exploded top perspective view of the contact lens cleaning and storage case of FIG. 7.
Figure 9:
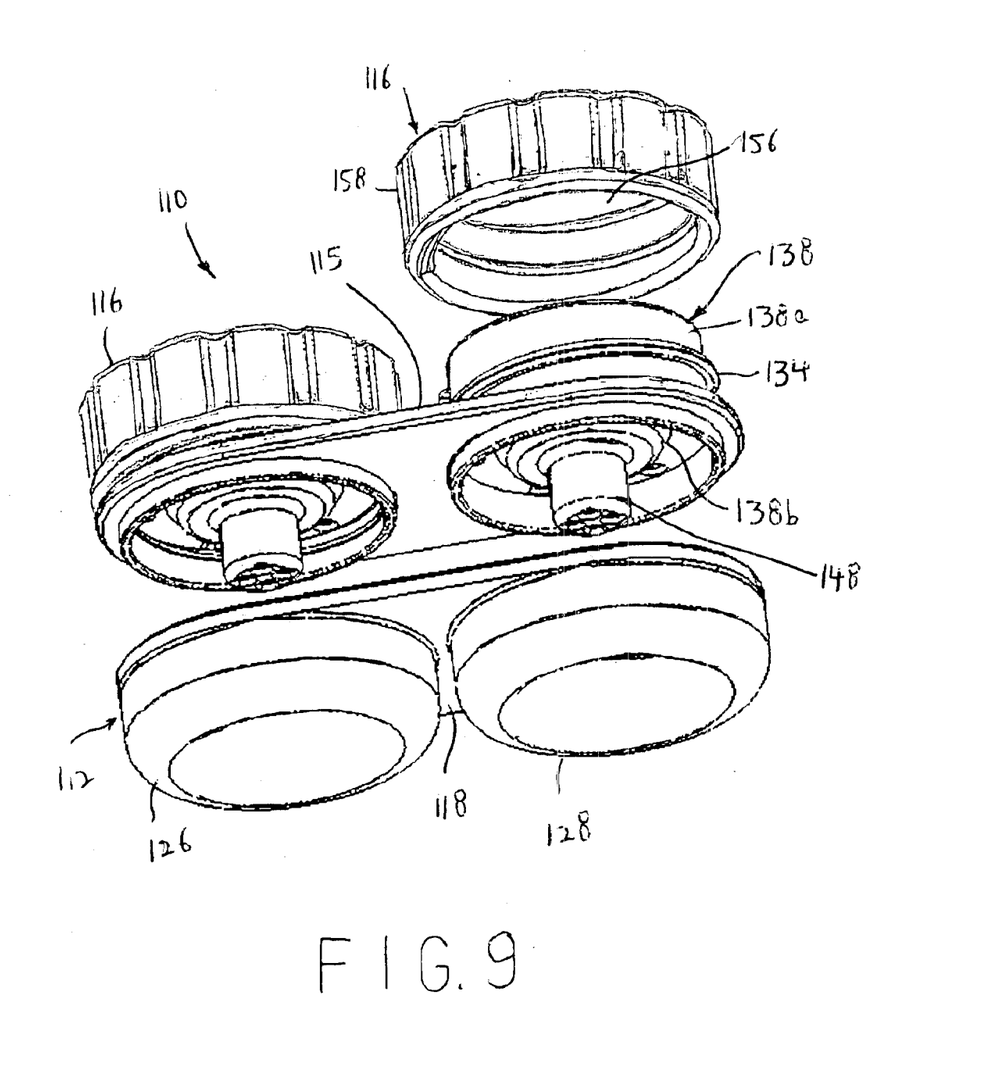
FIG. 9 is an exploded bottom perspective view of the contact lens cleaning and storage case of FIG. 7.

Specifically, contact lens cleaning and storage case 110 is made of a molded plastic material or any other liquid impermeable material and includes a base 112, a separator section 114 fixed to base 112, and caps 116.

Base 112 includes an oblong plate 118 having a general oval shape, and specifically has straight side edges and part-circular end edges, and is of a generally constant thickness. A molded cup-shaped container 126 is formed at one end of oblong plate 118 and hangs down therefrom, and a similar molded cup-shaped container 128 is formed at the opposite end of oblong plate 118 and hangs down therefrom, both containers 126 and 128 being open at upper ends thereof through oblong plate 118.

Containers 126 and 128 are preferably identical in construction, and in this regard, each container 126 and 128 has a generally cylindrical configuration with a radius in the range of approximately 2.0 to 3.0 cm and a height in the range of approximately 0.5 to 2.0 cm.

Figure 10:
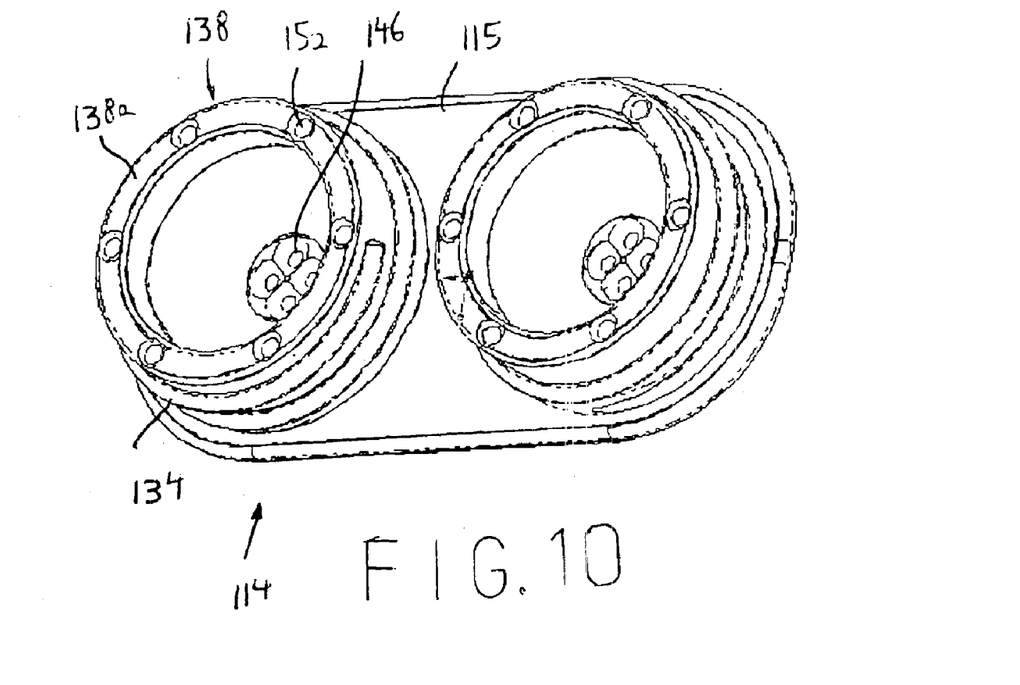
FIG. 10 is a top perspective view of the separator insert of the contact lens cleaning and storage case of FIG. 7.
Figure 11:
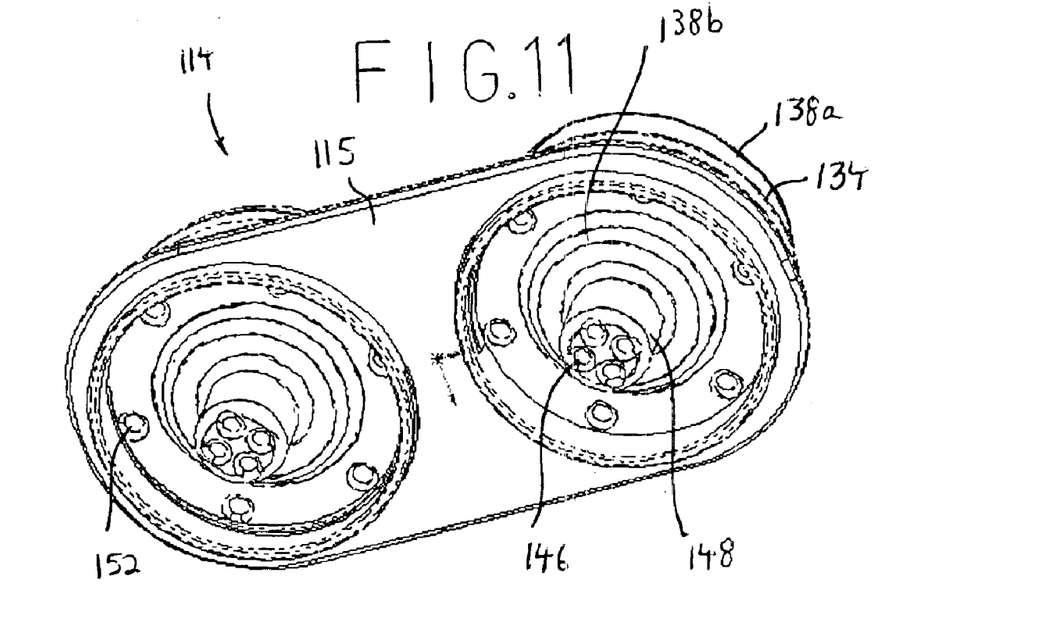
FIG. 11 is a bottom perspective view of the separator insert of the contact lens cleaning and storage case of FIG. 7.

Separator section 114 includes a plate 115 have substantially the same dimensions as oblong plate 118 so that when plate 115 is placed on top of oblong plate 118, plates 115 and 118 can be secured together by ultrasonic welding, adhesive or the like.

Separator section 114 further includes cylindrical, cup-shaped containers 138 extending from the upper surface of oblong plate 118 at opposite ends thereof, each formed by a cylindrical wall 138a at a position above oblong plate 115 and by a bowl shaped member 138b at a position below oblong plate 115 and forming a continuation of cylindrical wall 138a. A cylindrical drain tube 148 is molded to the lower end of each bowl shaped member 138b and is coaxially arranged relative to the respective container 138. Each drain tube 148 includes a plurality of through bores 146 which function as small drain openings. Although four drain openings are shown, the present invention is not limited thereby. As will be understood from the discussion which follows, the diameters of through bores 146 are such that liquid disinfecting solution placed in containers 138 will take approximately ten to fifteen seconds to drain, thereby providing sufficient time to clean the contact lens therein. Further, the outer diameter of through bores 146 is less than the inner diameter of containers 126 and 128 so that when contact lens cleaning and storage case 110 is inverted to drain the liquid, some of the liquid travels from containers 126 and 128 through bores 146.

The outer surface of each container wall 138a also includes threads 134 thereon. In addition, a plurality of drain openings 152 extend through each cylindrical wall 138a for providing a path for air removal when the containers 126 and 128 are filled and for draining the liquid in containers 126 and 128 after the contact lenses have been removed. Although drain openings 152 are shown as circular, they can be other shapes, such as oval or the like. Further, although six drain openings 152 are provided, the present invention is not limited thereby, and any other number can be used.

Each cap 116 includes a circular top wall 156 and an annular skirt 158 which extends downwardly from the outer edge of top wall 156. The inner surface of skirt 158 includes threads 160 which mate with threads 134 so that each cap 116 can be threadedly received on cup-shaped container 126 or 128 in a sealing manner, as is well known in the art. When a cap 116 is threaded on a cup-shaped container 126 or 128, circular top wall 156 of cap 116 seals elongated openings 152.

The operation is the same as that discussed above in regard to contact lens cleaning and storage case 10 of FIGS. 1–6.

Thus, with the present invention, the contact lens cleaning and storage case is provided with an arrangement for separating contaminants away from the stored lens. Specifically, it is required that the cleaning solution wash over the contact lens for a predetermined period and then drain to a different location, along with the contaminants. Further, the contaminants will not return to contaminate the stored contact lens in the case, even if the case is turned upside down. Thus, there is no possibility of recontamination of the lenses.

Further, because there is no recirculation of cleaning solution, there is no need for any bacteria killing mechanism, and there is no need for any harsh chemicals to clean and disinfect the lenses. The prcoess is very fast, and is completely hands free.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention defined by the appended claims.

What is claimed is:

1. A contact lens cleaning and storage case comprising:
   a base having at least one container section therein for holding a liquid;
   at least one lens holder positioned above a lower wall of the at least one container section, each lens holder having a lower section;
   a drain arranged in the lower section of each lens bolder for draining liquid from the at least one lens holder to the at least one container section, said drain including a plurality of restricted flow openings, said restricted flow openings:
      being of such a size to require the cleaning solution to wash over the contact lens for a predetermined period sufficient to separate contaminants away from the stored lens and then drain to the respective container section, and
      being positioned substantially only in a lowermost area of each lens holder to continuously provide clean solution to a lowermost convex side of a lens positioned in the respective lens holder; and
   at least one cap for removably covering the at least one lens holder.

2. A contact lens cleaning and storage case according to claim 1, wherein said at least one lens holder at least partially sits within said at least one container section.

3. A contact lens cleaning and storage case according to claim 2, wherein said at least at least one lens holder is removably secured to said base.

4. A contact lens cleaning and storage case according to claim 3, wherein each said lens holder includes a bowl shaped member for holding a contact lens, and the drain includes a drain tube extending downwardly from a bottom of said bowl shaped member.

5. A contact lens cleaning and storage case according to claim 1, wherein said drain includes a drain tube extending downwardly from the lower section of each said lens holder.

6. A contact lens cleaning and storage case comprising:
   a base having at least one container section therein for holding a liquid;
   at least one lens holder positioned above a lower wall of the at least one container section, each lens holder having a lower section;
   a drain arranged in the lower section of each lens holder for draining liquid from the at least one lens holder to the at least one container section, said drain including a drain tube extending from the lower section of each said lens holder and said drain tube includes a plurality of openings therein; and
   at least one cap for removably covering the at least one lens holder.

7. A contact lens cleaning and storage case according to claim 6, wherein said plurality of openings have diameters that restrict a flow rate of liquid therethrough so as to prevent draining of liquid from said at least one lens holder to said at least one container section in a time less than a predetermined time.

8. A contact lens cleaning and storage case according to claim 7, wherein the predetermined time is in a range between approximately ten and fifteen seconds.

9. A contact lens cleaning and storage case comprising:
   a base having at least one container section therein for holding a liquid;
   at least one lens holder positioned above a lower wall of the at least one container section, each lens holder having a lower section, said lower section of said lens holder including a plurality of openings;
   a drain arranged in the lower section of each lens holder for draining liquid from the at least one lens holder to the at least one container section, said drain including a drain tube extending from the lower section of each said lens holder, and said drain tube is connected to said lower section in surrounding relation to said plurality of openings; and
   at least one cap for removably covering the at least one lens holder.

10. A contact lens cleaning and storage case according to claim 9, wherein said plurality of openings have diameters that restrict a flow rate of liquid therethrough so as to prevent draining of liquid from said at least one lens holder to said at least one container section in a time less than a predetermined time.

11. A contact lens cleaning and storage case according to claim 9, wherein the predetermined time is in a range between approximately ten and fifteen seconds.

12. A contact lens cleaning and storage case according to claim 1, wherein said at least one lens holder includes at least one drain opening which provides fluid communication between atmosphere and said at least one container section.

13. A contact lens cleaning and storage case according to claim 12, wherein there are two said container sections and two lens holders, and said at least one cap includes two separate caps, each blocking a central open area and the drain openings of one lens holder when covering the respective lens holder.

14. A contact lens cleaning and storage case according to claim 12, wherein said at least one lens holder includes a bowl shaped member for holding a contact lens and a peripheral flange connected to said bowl shaped member in order to connect said at least one lens holder to said base, with said at least one drain opening being provided in said peripheral flange.

15. A contact lens cleaning and storage case comprising:
   a base having at least one container section therein for holding a liquid;
   at least one lens holder positioned above a lower wall of the at least one container section, each lens holder including:
      a bowl shaped member for holding a contact lens, the bowl shaped member including a lower section,
      a peripheral flange connected to said bowl shaped member in order to connect said at least one lens holder to said base,
      at least one drain opening provided in said peripheral flange a plurality of drain openings which provides fluid communication between atmosphere and said at least one container section, and a drain arranged in the lower section of each lens holder for draining liquid from the at least one lens holder to the at least one container section; and at least one cap for removably covering the at least one lens holder.

16. A contact lens cleaning and storage case according to claim 1, wherein said base has an upper surface, and said at least one lens holder has a lower facing surface in flush engagement with said upper surface and secured thereto.

17. A contact lens cleaning and storage case according to claim 16, wherein said at least one lens holder includes a peripheral wall that extends at least partially above said lower surface and at least one drain opening which provides fluid communication between atmosphere and said at least one container section being provided through said peripheral wall.

18. A contaminant separator for use with a contact lens cleaning and storage case of the type including a base having at least one container section therein for holding a liquid, and at least one cap, the contaminant separator comprising:

a lens holder positioned above a lower wall of the at least one container section, each lens holder having a lower section; and a drain arranged in the lower section of each lens holder for draining liquid from the at least one lens holder to the at least one container section, said drain including a plurality of restricted flow opening, said restricted flow openings:

being of such a size to require the cleaning solution to wash over the contact lens for a predetermined period sufficient to separate contaminants away from the stored lens and then drain to the respective container section, and being positioned substantially only in a lowermost area of each lens holder to continuously provide clean solution to a lowermost convex side of a lens positioned in the respective lens holder.

19. A contaminant separator according to claim 18, wherein said at least one lens holder is dimensioned to at least partially sit within said at least one container section.

20. A contaminant separator according to claim 18, wherein said at least at least one lens holder includes an arrangement for securing said at least one lens holder to said base.

21. A contaminant separator according to claim 18, wherein each said lens holder includes a bowl shaped member for holding a contact lens, and the drain includes a drain tube extending downwardly from a bottom of said bowl shaped member.

22. A contaminant separator according to claim 18, wherein said drain includes a drain tube extending downwardly from the lower section of each said lens holder.

23. A contaminant separator for use with a contact lens cleaning and storage case of the type including a base having at least one container section therein for holding a liquid, and at least one cap, the contaminant separator comprising:

a lens holder adapted to be positioned above a lower wall of the at least one container section, each lens holder having a lower section; and a drain arranged in the lower section of each lens holder for draining liquid from the at least one lens holder to the at least one container section, said drain including a drain tube extending from the lower section of each said lens holder, and said drain tube including a plurality of openings therein.

24. A contaminant separator according to claim 23, wherein said plurality of openings have diameters that restrict a flow rate of liquid therethrough so as to prevent draining of liquid from said at least one lens holder to said at least one container section in a time less than a predetermined time.

25. A contaminant separator according to claim 24, wherein the predetermined time is in a range between approximately ten and fifteen seconds.

26. A contaminant separator for use with a contact lens cleaning and storage case of the type including a base having at least one container section therein for holding a liquid, and at least one cap, the contaminant separator comprising;

a lens holder adapted to be positioned above a lower wall of the at least one container section, each lens holder having a lower section, said lower section of said lens holder including a plurality of openings; and a drain arranged in the lower section of each lens holder for draining liquid from the at least one lens holder to the at least one container section, said drain including a drain tube extending from the lower section of each said lens holder, and said drain tube is connected to said lower section in surrounding relation to said plurality of openings.

27. A contaminant separator according to claim 26, wherein said plurality of openings have diameters that restrict a flow rate of liquid therethrough so as to prevent draining of liquid from said at least one lens holder to said at least one container section in a time less than a predetermined time.

28. A contaminant separator according to claim 27, wherein the predetermined time is in a range between approximately ten and fifteen seconds.

29. A contaminant separator according to claim 18, wherein said at least one lens holder includes at least one drain opening which provides fluid communication between atmosphere and said at least one container section.

30. A contaminant separator according to claim 29, wherein said at least one lens holder includes a bowl shaped member for holding a contact lens and a peripheral flange connected to said bowl shaped member in order to connect said at least one lens holder to said base, with said at least one drain opening being provided in said peripheral flange.

31. A contaminant separator according to claim 15, wherein said base includes at least one recess and said at least one lens holder includes at least one catch mounted to said peripheral flange for engaging in said at least one recess in order to secure said at least one lens holder to said base.

32. A contaminant separator according to claim 18, wherein said base has an upper surface, and said at least one lens holder has a lower surface adapted to be in flush engagement with said upper surface and secured thereto.

33. A contact lens cleaning and storage case according to claim 32, wherein said at least one lens holder includes a peripheral wall that extends at least partially above said lower surface and at least one drain opening which provides fluid communication between atmosphere and said at least one container section being provided through said peripheral wall.

* * * * *